(12) United States Patent
Koehler et al.

(10) Patent No.: US 10,037,600 B2
(45) Date of Patent: Jul. 31, 2018

(54) BIAS-FREE REGULARIZATION FOR SPECTRAL PHASE-UNWRAPPING IN DIFFERENTIAL PHASE CONTRAST IMAGING

(71) Applicant: KONINKLIJKE PHILIPS N.V., Eindhoven (NL)

(72) Inventors: Thomas Koehler, Norderstedt (DE); Roland Proksa, Neu Wulmstorf (DE)

(73) Assignee: KONINKLIJKE PHILIPS N.V., Endhoven (NL)

( * ) Notice: Subject to any disclaimer, the term of this patent is extended or adjusted under 35 U.S.C. 154(b) by 55 days.

(21) Appl. No.: 15/309,223

(22) PCT Filed: Apr. 21, 2015

(86) PCT No.: PCT/EP2015/058566
§ 371 (c)(1),
(2) Date: Nov. 7, 2016

(87) PCT Pub. No.: WO2015/185259
PCT Pub. Date: Dec. 10, 2015

(65) Prior Publication Data
US 2017/0091933 A1  Mar. 30, 2017

(30) Foreign Application Priority Data
Jun. 2, 2014 (EP) .................................. 14170740

(51) Int. Cl.
*G06K 9/00* (2006.01)
*G06T 7/00* (2017.01)
*G06K 9/46* (2006.01)

(52) U.S. Cl.
CPC .......... *G06T 7/0012* (2013.01); *G06K 9/4671* (2013.01); *G06T 2207/10116* (2013.01)

(58) Field of Classification Search
None
See application file for complete search history.

(56) References Cited

U.S. PATENT DOCUMENTS 6,741,357 B2 * 5/2004 Wang .................. G01B 11/303
356/493
7,372,393 B2 * 5/2008 Yedidia ............... G01S 13/9035
342/195

(Continued)

FOREIGN PATENT DOCUMENTS

WO    2012/038857    3/2012
WO    2013083893    6/2013

(Continued)

OTHER PUBLICATIONS

Epple, et al., "Unwrapping differential x-ray phase-contrast images through phase estimation from multiple energy data", Optics Express, vol. 21, No. 24, Nov. 18, 2013.

(Continued)

*Primary Examiner* — Weiwen Yang
(74) *Attorney, Agent, or Firm* — Larry Liberchuk

(57) ABSTRACT

Methods and related apparatus (SP) to correct phase shift image data for phase wrapping artifacts. The data is detected at a detector (D) of an imaging system (IM) including interferometric equipment ($G_0$, $G_1$, $G_2$). In a phase unwrapping method that involves optimizing an objective function with regularization, a two-sage approach is proposed. The measured data is processed in one stage with regularization and in the other stage without regularization. This allows improving the accuracy of the corrected (phase unwrapped) phase shift data because an undesirable bias caused by the regularization can be avoided.

15 Claims, 5 Drawing Sheets

A)

B)

(56) References Cited

U.S. PATENT DOCUMENTS

| | | | |
|---|---|---|---|
| 8,433,739 B2* | 4/2013 | Ha | H04B 14/006 708/200 |
| 2012/0099702 A1 | 4/2012 | Engel | |

FOREIGN PATENT DOCUMENTS

| | | |
|---|---|---|
| WO | 2013091078 | 6/2013 |
| WO | 2013104966 | 7/2013 |

OTHER PUBLICATIONS

Pfeiffer et al in "Phase retrieval and differential phase-contrast imaging with low-brilliance X-ray sources," Nature Phys. Lett. 2, 258-261 (2006).

Weber et al in "Measurements and simulations analyzing the noise behavior of grating-based X-ray phase-contrast imaging", Nuclear Instruments and Methods in Physics Research A648(2011), pp. S273-S275.

Weber et al., "Noise in x-ray grating-based phase-contrast imaging", Med. Phys. 38 (7), Jul. 2011, pp. 4133-4140.

Gudbjartsson et al., "The Rician Distribution of Noisy MRI Data", in Magn. Reson. Med., Dec. 1995, 34(6), pp. 910-914.

Bioucas-dias, et al., "Absolute phase estimation: adaptive local denoising and global unwrapping", 2008.

Bioucas-Dias, et al., "Multi-frequency Phase Unwrapping from Noisy Data: Adaptive Local Maximum Likelihood Approach", SCIA 2009, LNCS 5575, pp. 310-320.

Ritter, et al., "Simultaneous maximum-likelihood reconstruction for x-ray grating based phase-contrast tomography avoiding intermediate phase retrieval", Physics Med, 2013.

\* cited by examiner

A) B)

A)

B)

BIAS-FREE REGULARIZATION FOR SPECTRAL PHASE-UNWRAPPING IN DIFFERENTIAL PHASE CONTRAST IMAGING

CROSS REFERENCE TO RELATED APPLICATIONS

This application is the U.S. National Phase application under 35 U.S.C. § 371 of International Application No. PCT/EP2015/058566, filed Apr. 21, 2015, published as WO 2015/185259 on Dec. 10, 2015, which claims the benefit of European Patent Application Number 14170740.6 filed Jun. 2, 2014. These applications are hereby incorporated by reference herein.

FIELD OF THE INVENTION

The invention relates to methods for processing measured phase shift data, to signal processing apparatuses, to computer program elements and to computer readable media.

BACKGROUND OF THE INVENTION

In a range of technical applications including the medical field phase contrast imaging has been recognized as superior to solely absorption based imaging techniques for its excellent soft tissue contrast. In some applications phase contrast imaging requires an interferometer mounted in an imaging apparatus. The interferometric set up allows extracting a certain phase shift of interference pattern which has been found to relate to the desired refraction and hence phase shift caused by the object to be imaged. Unfortunately, the phase shift data obtained via the interferometer may be ambiguous. This is because the interferometer has only a limited angular range. Any measurement beyond that range will be "wrapped" around into that range so that in effect it is not the phase shift itself that is observed but only the measured phase shift value "modulo the range". Phase wrapping is undesirable because it may cause visible artifacts in the phase contrast images. In order to combat this ambiguity a number of "phase un-wrapping" algorithms have been proposed in the past. It has been found however, that the accuracy of the un-wrapped phase data obtainable by existing algorithms is occasionally inaccurate.

SUMMARY OF THE INVENTION

There may therefore be a need to improve the accuracy when processing measured, phase shift data.

The object of the present invention is solved by the subject matter of the independent claims where further embodiments are incorporated in the dependent claims.

It should be noted that the following described aspect of the invention equally apply to the signal, to the signal processing apparatuses, to the computer program elements and to the computer readable media.

According to a first aspect of the invention there is provided a method for unwrapping phase shift data, comprising:
receiving phase shift data measured by a detector;
including the phase shift data as parameters into a non-convex or non-concave objective function without a regularization term;
finding critical points of said objective function;
finding, only among said critical points, a target critical point of a regularized objective function, said regularized objective function being formed from said objective function and a regularization term; and
outputting said target critical point as an estimate for unwrapped phase shift data.

According to a second aspect there is provided an alternative method for unwrapping phase shift data, comprising:
receiving phase shift data measured by a detector;
including the phase shift data as parameters into a regularized objective function formed from a non-convex or non-concave objective function and a regularization term;
finding critical points of said regularized objective function, said critical points including a lead critical point;
finding non-regularized critical points of said objective function without said regularization term;
choosing, from among the non-regularized critical points so found, a target point that is closer to the lead critical point than at least one of the at least one other non-regularized critical point; and
outputting said chosen target point as an estimate for unwrapped phase shift data.

In other words, the methods correct the input phase shift data for phase wrapping artifacts and output the so corrected data as the unwrapped phase shift data.

The objective function used herein is as known from the field of optimization theory. In other words the objective function is real valued function that maps elements of a domain of said function onto a real number. The objective function is also sometimes referred to as a utility or cost function depending on the context. The critical points of those functions are the arguments or positions in the domain of the function where the objective function assumes a local (or global) maximum or minimum. The critical points are therefore also called maximizer or minimizer according to context. Either one of maximization and minimization of the object function is envisaged herein. Searching for the critical points in either of the methods, amounts in one embodiment to solving the objective function for said critical points by otherwise known numerical algorithms.

The proposed methods allow avoiding or at least mitigating a bias effect introduced by the presence of the regularization term. The regularizer or regularization is likewise a real valued function that is usually solely a function of the elements in the domain of the objective function. It allows the enforcement of the desirable properties, for instance smoothness or "smallness" of the critical points to be searched for. It has been observed that if the objective function has multiple local minima (that is, the objective function is neither convex nor concave), the regularization term exerts a bias so as to shift the global minimum of the objective function into a correct range of the domain. This is desirable but the objective function also introduces an undesirable bias on the local extrema of the objective function towards said range (eg, small absolute values). As the unwrapped phase data sought for are among those local extrema, this bias carries through to the output of many phase unwrapping algorithms that are based on regularized optimization.

To overcome this bias effect, two alternative methods are proposed herein. According to one method, it is first the objective function without the regularization that is searched and then the result is applied to the regularized function. In the alternative embodiment, first the regularized function is searched and then the results are applied to the un-regularized objective function. In other words the sequence of the searching steps is reversed. In both methods the output (that is, the un-wrapped phase shift data) are ultimately points of the un-regularized objective function. In other words the critical points of the regularized objective function are not as such returned as un-wrapped phase shift data. Rather the critical points of the regularized objective function are used as a guiding means to select from the critical points of the un-regularized objective function. In this way, the bias in the searching step caused by the presence of the regularization term can be avoided or at least mitigated and yet one is still able to take account of the regularization requirements. In yet other words, the method allows striking a balance between observing the need to have regularization and to avoid or mitigate the bias so caused by said regularization terms.

According to one embodiment the objective function is a likelihood function in respect of the measured data. The probability density underlying the likelihood function is any one of a wrapped Gaussian density, a von Mises density or other suitable probability densities that lend themselves for probabilistic modelling of "directional" data such as angular data.

But that is not to say that the objective function must necessarily be of probabilistic origin. The proposed method is applicable to any phase unwrapping algorithm that uses optimization of an objective function, no matter how the objective functions is obtained, be it by statistical/probabilistic or other signal modelling approaches.

In the method according to the second aspect, the target point is closest (when measured by a suitable distance measure) to the lead point according to one embodiment. However this is not mandatory, as there are alternative embodiments envisaged where it is sufficient for the target point to be merely within a pre-defined proximity of the lead point so may not be the "closest" to the lead point when all the non-regularized critical points are considered.

In one embodiment the regularization term is a Tikhonov regularizer. This allows accounting for the fact that the measured data may be under-sampled due to a limited spatial resolution of the detector.

According to one embodiment, in either one of said methods, the measured data at a given pixel is processed independently from data measured at a (or any or all) neighboring pixel. In other words, wherein said method does not rely on data measured at a neighboring pixel of a given pixel of the detector D when said method is applied to the data measured at said given pixel.

The "lead" critical point is one at which the (regularized) objective function returns a "better" value than at least one of the at least one other critical point does when evaluated by the objective function. The qualifier "better" depends on the optimization task at hand. For instance, in a minimization problem, the lower the value the better. Conversely, in a maximization problem, the larger the value the better. In particular and according to one embodiment, the lead critical point may be one at which the objective function assumes the largest or smallest value of all the other critical points. But this is not mandatory, as alternative embodiments are envisaged where it is sufficient for the lead point to merely return a value better than a pre-defined threshold or return a value better than a pre-defined number of critical points do.

A "critical point" as used herein is one where the objective function assumes a local (or a global) minimum or maximum. As used herein, for any given optimization problem, the "critical point" is throughout either a local minimum or a local maximum. A mixed situation, where, for a given optimization, a critical point is once a local minimum and then a local maximum, is not envisaged herein.

DETAILED DESCRIPTION OF EMBODIMENTS

Figure 1:
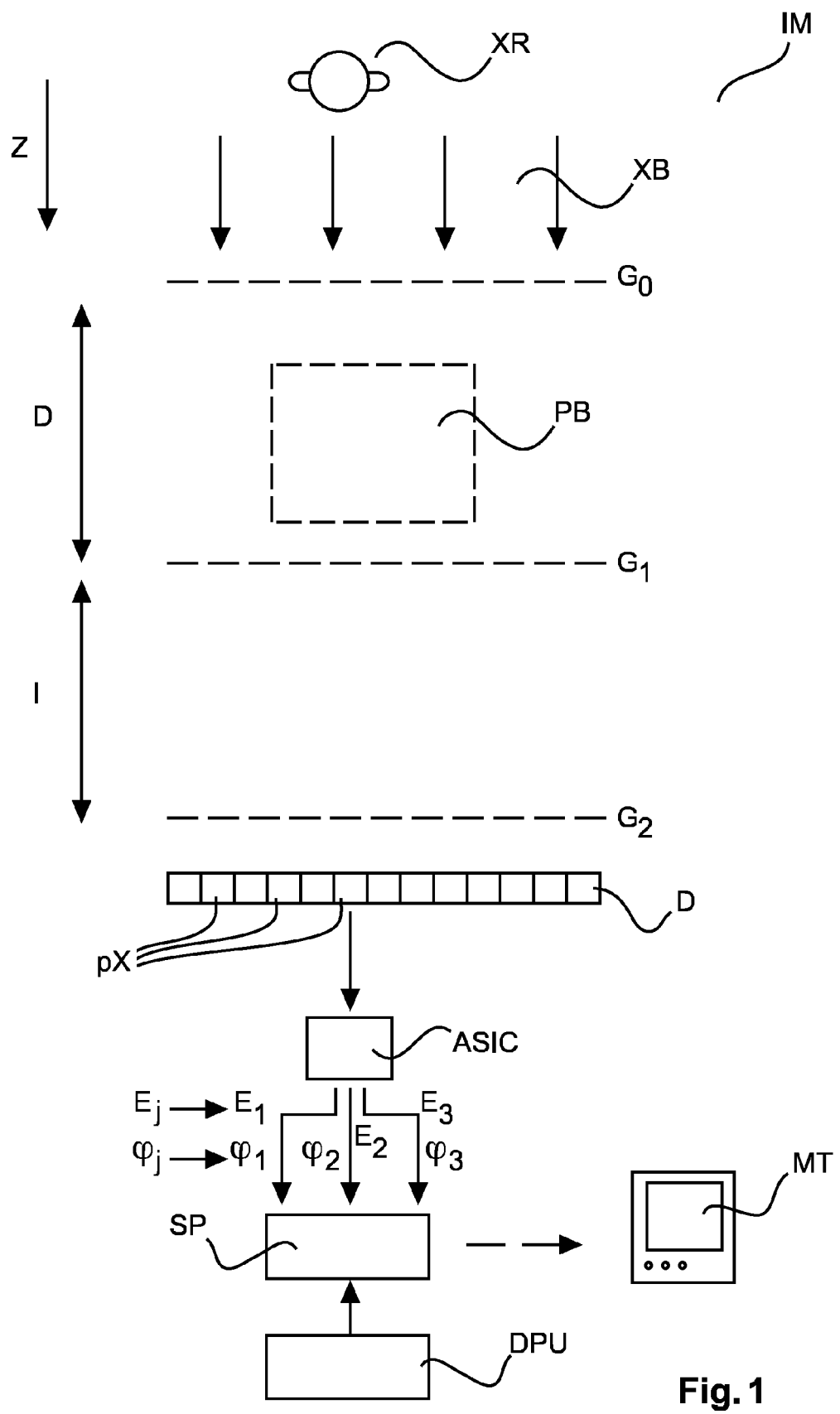
FIG. 1 shows an imaging arrangement for spectral differential phase contrast imaging.

FIG. 1 shows basic components of an imaging system IM with phase contrast imaging capabilities, in particular differential phase contrast imaging (DPCI). There is an X-ray source XR for generating X-ray radiation waves XB that, after passage through an examination region, are detectable by detector pixels px of a detector D. The phase contrast imaging capability is achieved by an interferometer arranged between the X-ray source XR and the radiation sensitive detector D.

The interferometer (which in one unlimiting embodiment is of the Talbot type or of the Talbot-Lau type) includes two $G_1$, $G_2$ (Talbot type) or more, preferably, three gratings $G_0$, $G_1$ and $G_2$ (Talbot-Lau type). The first attenuation grating $G_0$ at the X-ray source side has a period $p_0$ to match and cause spatial coherence of the X-ray radiation wave front emitted at the X-ray source XR.

An absorption grating $G_1$ (having period p1) is placed at distance D from the X-ray source and causes an interference pattern with period p2 further downstream. Said interference pattern can be detected by detector D. Now, when a sample (to be imaged) is introduced in the examination region between the X-ray source and the detector, the phase of the interference pattern is then shifted. This interference pattern shift $\Delta\varphi$ (as has been reported elsewhere, for instance in F M Epple et al, Unwrapping differential X-ray phase contrast images through phase estimation from multiple energy data, OPTICS EXPRESS, 2 Dec. 2013, Vol 21, No 24) is proportional to the gradient of the phase shift $\Phi\Delta$ due to the accumulated refraction along respective paths through the sample (hence the name DCPI). In other words, if one were then to measure the phase change of the interference, this would allow to extract the shift (or gradient) of the phase shift that is caused by refraction in the sample.

Unfortunately the phase shift of the interference pattern is typically too small to be directly spatially resolved. The resolution powers of most X-ray detectors would not allow this. Therefore in order to "sample" this interference pattern phase shift, a second attenuation rating $G_2$ with the same period p2 as the interference pattern is placed at a distance 1 from grating $G_1$. The actual extraction of the interference pattern phase shift (and hence that of the phase gradient caused by the sample) can be achieved in a number of different ways according to different embodiments that are all envisaged herein.

In general what is required for the differential phase extraction is a relative motion between the detector D and at least one of the gratings. This can be achieved in one embodiment by using an actuator to laterally (that is along x direction perpendicular to the gratings), move for instance, analyzer grating $G_2$ across different, discrete grating positions and then measure at each grating position the intensity at each pixel px. The intensity at each pixel will be found to oscillate in a sinusoidal fashion. In other words, each pixel records a time series of different intensities (at the respective pixel) as a function of time (or better as a function of the different grating positions) during motion of the analyzer grating G2. This approach ("phase-stepping") has been described by F. Pfeiffer et al in "Phase retrieval and differential phase-contrast imaging with low-brilliance X-ray sources," Nature Phys. Lett. 2, 258-261 (2006).

As described for instance on page 29104, equations (1a), (1b) in the Epple reference cited earlier, the oscillating intensity signal at each pixel px "encodes" amongst other quantities the desired phase shift of the interference pattern $\Delta\varphi$ ($\sim\Phi\Delta$) (phase shift, hereinafter simply referred to as $\varphi$).

The interference pattern shift $\Delta\varphi$ can be obtained by processing the detector signals per pixel px into numerical form by data acquisition circuitry (not shown) which includes in particular A/D conversion circuitry. The numbers are then processed by a Fourier Analyzer module (not shown) or by a module that is configured to perform suitable curve fitting operations to obtain the measured phase shifts $\Delta\varphi$, per pixel. The collection of these parameters can then be processed by a processing unit.

Detector D in the imaging system IM of FIG. 1 is of the photon counting type. The detector D includes circuitry ASIC that affords the photon counting and energy resolving capability of the detector arrangement. This capability allows spectral imaging as each energy response can be associated with a specific base material (bone, water, lipids, contrast agent, etc) of which an imaged object is thought to be composed. A pulse picked up at any given pixel px is compared with certain energy threshold values (also referred to as "bins") that represent different energy levels $E_j = E_1, E_2, E_3$. If the pulse exceeds a certain threshold a counter for said energy threshold is then set and the signal is processed, e.g., by the Fourier analyzer into a phase shift $\varphi_j$ for a certain energy $E_1, E_2,$ or $E_3$.

In other words in the photon energy resolving embodiment of detector, phase shift data $\varphi_j$ measured at different energy levels $E_j$ is provided through different energy channels $E_1$ to $E_3$ (only three such energy levels $E_1, E_2$ and $E_3$ are shown in the Fig. but this is purely for illustrative purposes and any other number of energy levels greater than two is envisaged herein).

The phase shift angles $\varphi_j$ of the interference pattern for each energy channel are then processed per pixel by a signal processor SP as will be described in further detail below to unwrap the phase ambiguity. Single processor SP can be run on a digital processing unit such as a work station DPU. The unwrapped phase angles may then be rendered by suitable imaging software into phase contrast images for display on a screen MT or may otherwise be processed or stored.

Figure 2:
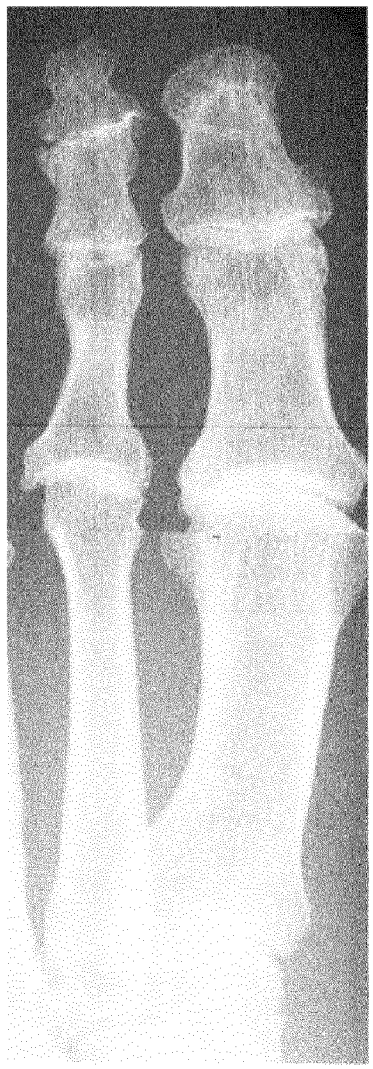
FIG. 2 shows an example of image noise or artifacts caused by phase wrapping.
Figure 2:

Phase wrapping, as briefly mentioned, is phenomenon which may occur inter alia in differential phase contrast imaging since the dynamic range of the interferometer is usually limited to a certain angular range, for example between $-\pi$ and $\pi$. In other words the interferometer (that is the system of the three (or at least two) gratings $G_0$ to $G_2$) does not actually allow measuring the phase shift of the interference pattern as such but only the true phase shift "modulo $2\pi$": the interferometer's response to an out-of-range phase shift corresponds to "wrapping" the true phase shift (expressed as a length in radian) around the unit circle as many times as the length admits and then reading off the angular position on the unit circle's circumference where the wrapped end of the length comes to lie. The information on the number of windings is lost. It is only the said angular position of the end that is available as the interferometer's response. A phase unwrapping algorithm aims at recovering the lost information from the wrapped up phase and additional information or model assumption. This loss of information is undesirable as it introduces an "artificial" discontinuity in the phase contrast image data which in turn leads to image noise which can potentially obscure crucial details in the imagery. Exemplary phase contrast imagery in panes A) and B) of FIG. 2 shows what can go wrong. FIG. 2A) on the left shows a phantom body (in this case a human foot imaged at 25 keV whose structure provokes refraction gradients which will exceed the dynamic range of the interferometer. Pane A) shows a conventional absorption X-ray image. The right pane B) shows a corresponding phase contrast image. The pair of arrows point to image portions with noise accumulation or artifacts caused by the phase wrap discontinuity. The other image portions in image B) appear sufficiently smooth so no phase wrapping is present there. The phase wrapping leads to even more disturbing artifacts during subsequent processing such as reconstruction or when the phase wrapped data is combined with an absorption contrast image data.

It is therefore desirable to resolve the ambiguity with respect to the phase shift to unwrap the measured (angular) phase shift data. It has been found that in many detector based systems it cannot be guaranteed that the differential phase contrast image is actually sampled in accordance with Shannon's sampling condition. The spatial resolution of the detector (that is the, inter-space between neighboring pixels) usually is not small enough to satisfy the (spatial) sampling theorem. This fact has been found by Applicant to seriously undermine the fidelity of results if one is to use standard phase un-wrapping algorithms.

Figure 3:
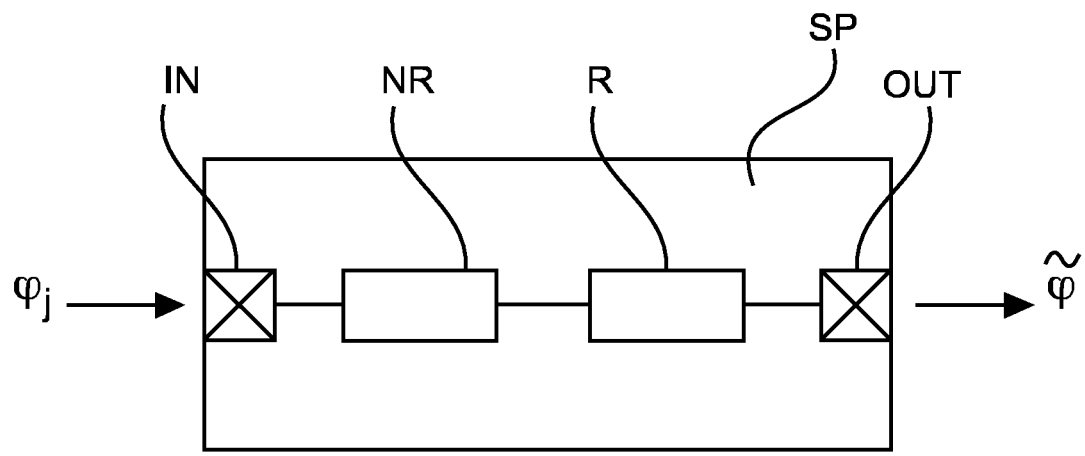
FIG. 3 shows block diagrams of signal processors according to different embodiments.
Figure 3:
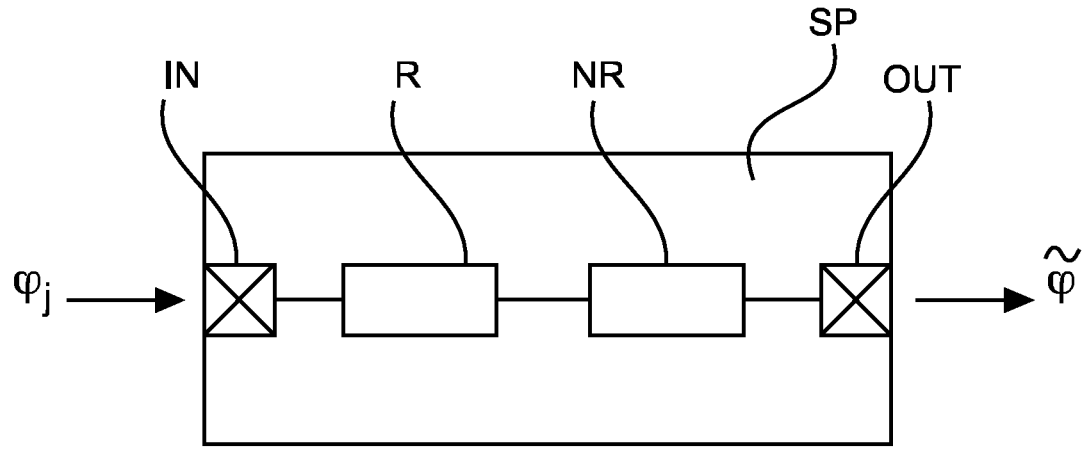

With reference to FIG. 3 there are shown two embodiments A, B of the signal processor SP for resolving phase ambiguities, that is, both are configured to operate as a "phase un-wrapper". More particularly, the signal processor as proposed herein is intended for combination with existing phase un-wrapping algorithms which involve solving an optimization problem.

An example of such phase unwrapping algorithm is described in the previously cited Epple reference on page 29105, equation (5). Like other phase unwrapping algorithms, Epple describes finding maximizers or minimizers of a certain objective function $f$. The objective function is in general a cost function or a utility function that maps elements of a predefined admissible range (the function's "domain", in this case angular values measured in radian) to a number. The objective function is a scalar valued function that defines a curve in 2D or a surface in 3 or higher dimensions which in general includes a number of local minima or maxima. The sought after points in optimization are those where a local minima or maxima (collectively referred to as local "extrema") occurs. Those points will be referred to as maximizers (for maximization problems) or minimizers (for minimization problems) or collectively as "critical points" but, for a given optimization problem, the critical points are either local minima or maxima but not both. Whether or not a point is a "critical" one depends not only on what the function does but also on the particular domain, that is, on the range of elements the function is applied to or is evaluated at. The domain may be continuous (e.g., the real numbers) but when one restrict said function to a discrete sub-domain (all integers say) than one may get different results on which point is or is not a critical one. A sufficient but not a necessary condition for a critical point is one where the objective function is differentiable and its gradient or derivative of the function vanishes. A simple sampling of the neighborhood of the objective function allows for deciding whether the found critical point is a minimizer or a maximizer.

In the following, when a maximization problem is considered (that is, finding, searching or solving for maximizers) it is understood that all that has been said equally applies to the opposite problem, that is, a minimization problem as each maximization problem can be re-written as a minimization problem and vice versa. In other words, the methods and signal processors as proposed herein are envisaged for either one of a maximization or minimization.

Referring back to the particular case of phase un-wrapping algorithms, the measured and potentially wrapped phase angles are applied to an objective function of the particular type under consideration, and a numerical algorithm then searches for the critical points. The critical points may then be output (possibly after some rescaling) as the un-wrapped phases which can then be passed on to a reconstructor for CT image reconstruction or some other image processing backend.

Yet more particularly and as exemplary described in Epple, the objective function on which the proposed signal processor SP operates, may be based on a signal modelling approach, for example a statistical approach such as Maximum-Likelihood (ML) or other considerations.

The objective function is formulated depending on the signal modelling approach taken and the measured (and possible wrapped) phase shifts at the different energy levels $E_1$, $E_2$, $E_3$ are applied as parameters to the objective function. The corresponding unwrapped phase shift data are included in the objective function as free variables one wishes to solve or "search" for by suitable numerical algorithm or technique. In other words, the objective function relates the measured, possible wrapped, phase shift data to the (yet unknown) unwrapped phase shift data. The signal processing apparatus SP operates to compute the unwrapped phase shift data by applying the suitable numerical algorithm in a manner to be explained in more detail below at FIGS. 3 and 5.

As an extension of the above, a number of known phase un-wrapping algorithms (such as the one in Epple) do not merely solve for critical points of an objective function but solve for critical points of a regularized objective function. This regularization comes about by using a regularizer term R. A regularizer term or sometimes referred to as a penalty function is a term that is arithmetically combined with the objective function under consideration to form a regularized objective function. The penalty or regularization term is used to enforce certain desirable properties of the solution (the critical points that is) to the optimization problem. For instance one may wish certain smoothness conditions to be met which would exclude other possible solutions if one were to use the objective function without the regularization term. In other embodiments one may wish to favor "small" solutions to the optimization problem over large ones, where smallness is measured by a suitable norm such as $L_1$ or $L_2$ incorporated in the penalty term.

Figure 4:
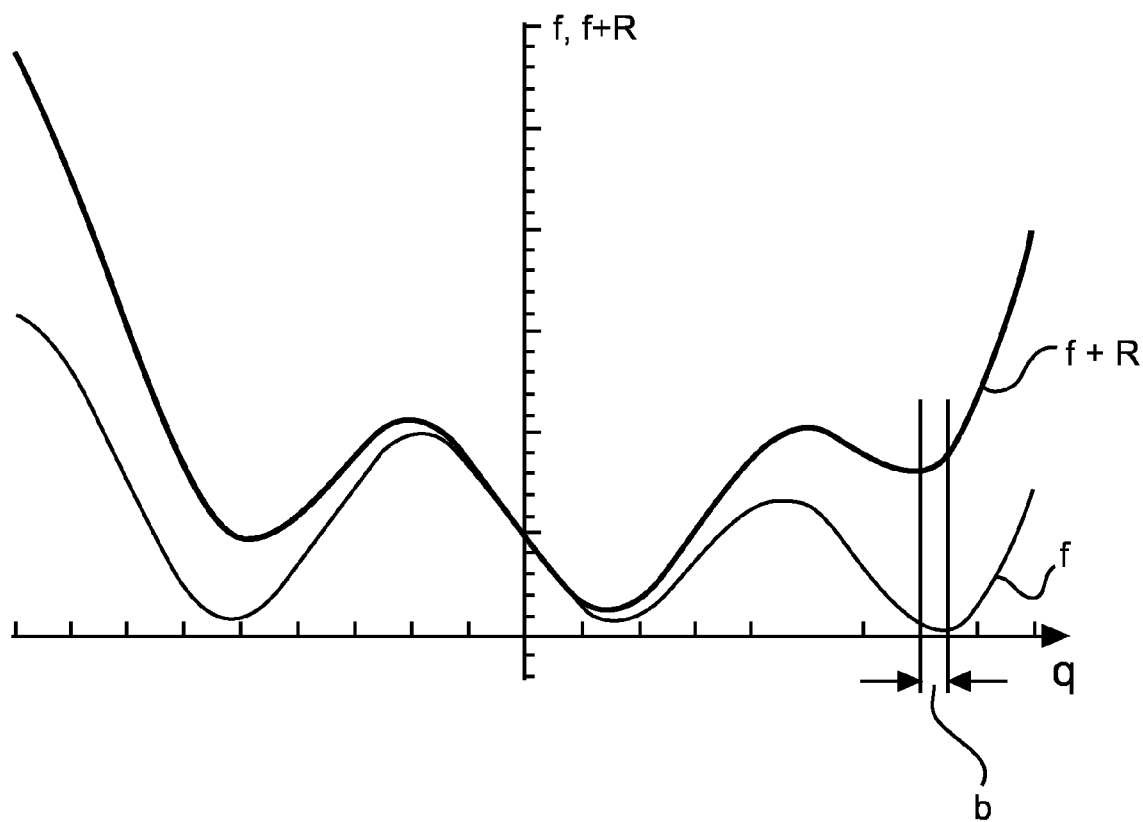
FIG. 4 graphs of a regularized and an un-regularized objective function.

An effect of the regularizer term R on the objective function $f$ is diagrammatically displayed in FIG. 4, where a minimization problem is considered. FIG. 4 shows the graph of an un-regularized objective function $f$ having different local minima and maxima, in other words the function $f$ is non-convex and it turns out that the method and signal processor as proposed herein is of particular application for such non-convex/non-concave functions. As can be seen a local minimum of the function $f$ occurs at a certain element of the function's domain (which in this case is taken to be the range of phase angles q=φ). If one now combines this function with a regularization term R (for instance by forming the functional sum of the two) to form a regularized objective function $f$+R, its graph/surface is effectively squeezed towards the origin. The intention for using regularization terms R is (in a minimization context) to "penalize" local minima in proportion to their distance from the origin. In other words, "small" minima (that is, those closer to the origin) are favored. But, unfortunately, there is also another, unintended effect: the application of the regularizer R also causes a bias b in that the critical points themselves are shifted to the origin. This bias has been observed sometimes to cause inaccuracies. The signal processor according to FIG. 3 as proposed herein operates to remove this bias and to so retain the benefits of having regularization function but with the added benefit that the returned solutions are more accurate to the original problem. Again, all that has been said in FIG. 4 about minima mutatis mutandis applicable to maximization and non-concave functions and these embodiments are envisaged herein.

Briefly, and as can be seen in FIG. 3, the embodiments A), B) of signal processor SR includes suitable interfaces IN and OUT to, respectively, receive per pixel the (possibly phase wrap corrupted) measured phase angles $φ_j$ and output un-wrapped phase angle estimates $\bar{φ}$ (for said pixel) in which the phase wrapping corruption has been removed or at least mitigated for some or all measured values.

Signal processor SP includes at least two optimization modules R and NR. One module R, operates as an optimizer to search for critical points of a regularized objective function, whereas the other module NR solves or operates to search for critical points of a non-regularized objective function.

Broadly, as schematically shown in FIG. 3A), B) the sequence of the two optimization modules NR and R in the processing pipeline can be reversed. In other words, in the embodiment of Fig. A the phase angles $φ_j$ are first applied to an objective function that is not regularized and further downstream the results of this first stage optimization are further processed at a second stage where the objective function is regularized. In the embodiment B) of FIG. 3 this processing pipeline is reversed in that the received phase angles are first applied to an objective function that is regularized and the output therefrom is then fed into the second module where the objective function is not regularized. In short, what is proposed herein is a two-stage signal processing module that includes two optimizers, one for optimization in respect of the objective function without regularization term and one for optimization with respect to the objective function with a regularization term. The two optimizer modules can be applied in either order. Operation of signal processor SP of FIG. 3 will now be explained, first with reference to the flow chart A) in FIG. 5.

At step S305 the (potentially phase wrapped) energy resolved phase angles $φ_j$ are received as data "seen" at detector D through the interferometric imaging equipment $G_0$-$G_2$ of imaging system IM.

At step S310 the so received phase shift data is applied to an objective function F without the regularization term, that is, placeholders for the parameters are populated with the measured data. As has been hinted at earlier, the complication with the shift of the critical points towards the origin caused by the presence of the regularization term can only apply when there are two or more minima in the surface of the objective function. Therefore the following invention is of particular application to objective function that is non-convex (or non-concave, depending on whether the optimizer operates to perform a maximization or a minimization).

Figure 5:
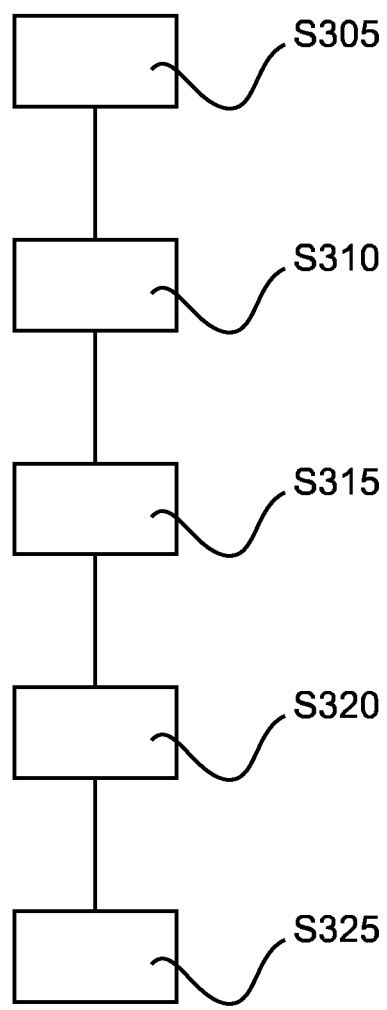
FIG. 5 shows flow charts of methods according to different embodiments of processing phase shift data.
Figure 5:
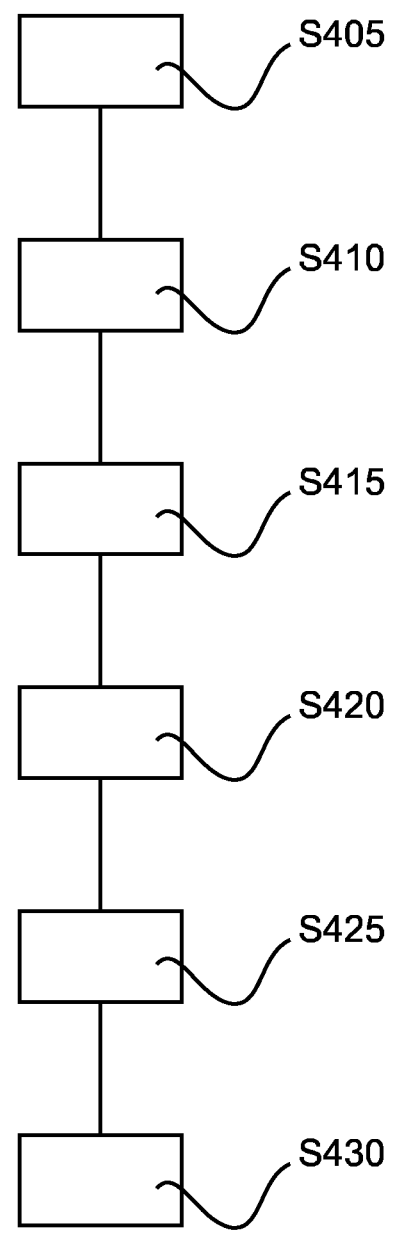

Referring back to the flow chart A) of FIG. 5, at step S315, signal processor SP's first optimizer module NR searches for the critical points of said (non-convex or non-concave) objective function. Notably, no regularizer term R is involved at this stage in the processing pipeline. The search or solving operation at S315 can be achieved by any of existing numerical minimization or maximization algorithms that effectively solve for those critical points. Examples that are envisaged herein are the downhill simplex method, a (nonlinear) conjugate gradient method, Newton-Raphson methods etc. A suitable one can be chosen to adapt for the ill-posedness in relation to the specific objective function at hand whose structure is in general determined by the signal model chosen. An exemplary embodiment is a statistical approach of the ML approach (given a suitable type of probability densities) where, for numerical reasons, the negative log of the likelihood function is usually optimized. In the present detector context, (wrapped) Gaussian or von Mises type densities are modeled into the signal model according to one embodiment.

The critical points so found are then forwarded to stage S320 to second optimizer R where said critical points are now processed in respect of a combined objective function, that is, a regularized objective function that is formed from the previous objective function at stage S315 of module NR and the regularization term. However, this time as opposed to step S310, the previously continuous domain is now discrete, that is, restricted to the discreet space of the set of critical points found at Step S315. In other words, in step S320 a search is conducted only among the critical points to reveal a target critical point of the regularized objective function. One way to achieve the now regularized optimization in step S320 is to evaluate the regularized objective function at the discrete and finite set of critical points and finds the one where the objective function assumes or "returns" the least value or at least where the objective function assumes a value less than a pre-definable acceptability threshold. If there are more points that fulfill this condition, that is, if more than one of the critical points returns a value of the regularized objective function that falls under said threshold, then a random experiment may be conducted to return a single one of said points that are presented as qualifying points in a user interface to the human user for final selection. For instance, sample phase contrast images can be generated for each of the qualifying critical points by replacing the previous, measured phase shift values with a respective one of the qualifying critical points and the user can then examine the sample image for visual smoothness to so support a final selection.

At step S325 the target point is output for the relevant pixel as the un-wrapped phase shift datum either directly or after some conversation or scaling which depends on the particular optimization algorithm and/or objective function used.

According to one embodiment the above steps S305-S325 are processed independently (but possibly in parallel or in serialized fashion) for each single pixel data. In other words, an evaluation of neighborhood data for any given pixels or process is not involved in the present approach. This is to be distinguished from other approaches such as disclosed in Applicant's WO 2012/038857 where, in order to arrive at an un-wrapped phase value for a pixel, the evaluation of neighboring pixel values for said pixel are required.

Reference is now made to flow chart B) in FIG. 5 that corresponds to the method implementable by a signal processing unit according to embodiment b) of FIG. 3.

This method is similar to the previous method in embodiment A), but now the sequence of steps S315 and S320 are essentially reversed in the processing pipeline.

In more detail, at step S405, the phase shift data for any given pixel is received.

The measured data is then applied at step S410 to a regularized objective function as implemented by module R. The regularized objective function is formed by a non-convex objective function and a regularization term similar to what has been explained above at step S310.

In variance to step S315, a search is conducted at step S415 to find critical points first of the regularized objective function using module R first in the processing pipeline. Among the critical points found is a "lead" critical point, that is, one that fulfils the regularized objective function "best" or is at least better than some or all of the other critical points so found. For instance the lead critical point may return the least value when the regularized objective function is evaluated at said lead critical point or returns the highest value when so evaluated. In other words, the lead critical point "leads" in two senses. It is leading in terms of attracting the least cost or having the highest utility depending on how the optimization task is formulated. But said lead points "leads" or guides the search to the desired un-wrapped phase shift data as will now be explained with reference to the next two steps S420, S425. In some embodiments the lead point may not be the best globally but may be merely required to be better, that is, returns a more favorable response to the regularized objective function than the majority of the remaining critical points or may return a response better than a pre-defined threshold.

Process flow now passes on to module NR at Step S420, to find "non-regularized" critical points, that is, critical points of the unregularized objective function, that is, the objective function in step S415 is now optimized in isolation without the regularizer term.

Then in step S425, the un-regularized optimization problem is solved by choosing from among the non-regularized critical points found in step S420, the one that is closest to the lead critical point found back in step S415 when solving the regularized optimization problem. The closeness is measured by some suitable norm such as L1 or L2. In some embodiments, there may be more than one "closest" point because it is merely required for the non-regularized critical points to be closer to the lead critical point than a pre-definable distance threshold. In the latter case, a random algorithm may be run to render the algorithm conclusive. Alternatively, a user interface is presented for ultimate selection as described above for embodiment A).

At step S430 then the point chosen in step S425 is then output as the unwrapped phase shift data possibly after application of a suitable conversional or scaling operation.

As will be appreciated from the two embodiments in both cases the output points are always those of the un-regularized optimization problem. However, the regularized optimization problem is still conducted to ensure that the regularization requirements are met. But the critical points found by optimizing the regularized version of the objective function are used only as a guiding means or "cues" to select from the unregularized critical points searched in respect of the un-regularized objective function, This ensures that the final results output at steps S325 or S430 are each without bias due to the influence of the regularization term.

As briefly mentioned above the specific form of the regularization term and the objective function will depend on the specific phase un-wrapping algorithm and/or the underlying signal model used. The present method may therefore be thought of as an add-on to existing phase-unwrapping algorithms that involve an optimization problem in respect of a non-convex or non-concave objective function.

Also, the numerical techniques used in the two modules R and NR to find the critical points may or may not be the same.

For instance, according to one embodiment and similar to what has been described by Epple the objective function with the regularization term R may have the following structure:

$$l(M) = -\sum_w \frac{1}{\sigma_w^2} \cos\left(\phi_m - \frac{M}{E_w^2}\right) + \lambda R(M) \quad (1)$$

wherein:
w indicates the different energy bins,
$\phi_m$ is the measured, potentially wrapped phase shift,
M is the to be estimated unwrapped phase shift $\tilde{\phi}$,
$E_w$ is the effective energy of the energy bin w,
$\sigma_w^2$ is the standard deviation of the measured phase shift $\phi_m$,
R is a regularization function, and
$\lambda$ is a regularization parameter to control the strength of the regularizer R's response.

The model parameters $\sigma_w^2$, $E_w$, $\lambda$ may be obtained through calibration measurements and is $\lambda$ is adjusted in test measurements for best results.

The underlying signal model in (1) exploits the well-known energy dependence of the phase gradient for the un-wrapping problem although the above model can still be used with monochromatic radiation as described in Epple.

The above objective function $l(M=\phi)$ as per (1) is derived from a maximum likelihood approach. The unwrapped phase shift data is estimated phase t using a maximum likelihood function. More specifically the phase gradient data is estimated by minimization of the log of said maximum likelihood function.

It has been assumed that the phase data measure detector is governed by a von Mises density. However other densities may also be included herein, for instance instead, wrapped Gaussian density may be assumed. T Weber et al in "Measurements and simulations analyzing the noise behavior of grating-based X-ray phase-contrast imaging", Nuclear Instruments and Methods in Physics Research A648 (2011), pp S273-S275 confirms (see FIG. 4 of Weber) that von Mises describes phase shift measurements with sufficient accuracy and T Weber et al discuss in "Noise in x-ray grating-based phase-contrast imaging", Med. Phys. 38 (7), July 2011, pp 4133-4140 the respective variances of the von Mises distribution that can be used to estimate for instance $\sigma_w^2$ in (1) above. Other options for suitable densities are described in equation (5) by H Gudbjartsson et al in "The Rician Distribution of Noisy MRI Data", in Magn. Reson. Med., 1995, December, 34(6), pp 910-914.

It will be appreciated that depending on the density or distribution type that is used to model the statistics of the measured data, the likelihood function will have a different structure from the (1) and may call therefore for other numerical techniques to find the critical points. However, it will be appreciated by those skilled in the art that the above two stage regularization and non-regularization approach can be applied to any objective function whether or not it be derived from a maximum likelihood approach. For instance, objective functions based on other numerical methods are also envisaged herein.

As can be seen the regularization term is solely a function of the specific sample point M under consideration. According to one embodiment the regularization term is a Tikhonov regularizer. This allows accounting for the fact that the entire phase contrast image of phase gradients (See pane B) in FIG. 2) may suffer from aliasing which makes regularization by a smoothness constraint in the image domain disadvantageous. Instead, the Tikhonov regularization is proposed which penalizes the square of M, thus favoring small values for the phase gradient M.

As an example, applying step S315 of method A) of FIG. 3 to the objective function (1) asks for finding the (in this case) local minima in an admissible range/domain for the physical free variable M (=$\phi$) of the un-regularized log-likelihood function:

$$l_0(M) = -\sum_w \frac{1}{\sigma_w^2} \cos\left(\phi_m - \frac{M}{E_w^2}\right) \quad (2)$$

Notably, the regularizer is absent in step S315.

The positions of the local minima found numerically are denoted by $M_1, M_2, \ldots, M_n$. Since no regularization has been applied in (2), the best estimate for the true value of M, which is among these values, does not suffer from bias. Regularization is applied in the follow up step S320, where the proper, "target" local minimum is obtained from the discrete minimization problem:

$$k = \operatorname{argmin}(l_0(M_i) + \lambda M_i^2) \quad (3)$$

This optimization problem is very similar to the original regularization problem (2), except that now only the bias-free local minima $M_1, M_2, \ldots, M_n$ of the un-regularized log-likelihood function are considered. In other words, the continuous domain considered in the optimization of (2) is no restricted to the discrete domain defined by the subset $\{M_1, M_2, \ldots, M_n\}$. Thus, the final value $M_k$ of the phase unwrapping will not suffer or will suffer less from a regularization induced bias.

In the alternative, if one were to apply the alternative method as as per B) in FIG. 3, one first solves equation (1) in the continuous domain for the critical points and establishes the lead critical point by evaluating (1) at those critical points. One then solves (2) again in the continuous domain to solve for the unregularized critical points. One then chooses as the output a point from said unregularized critical points that is closest or at least is sufficiently close (against a distance threshold) to the lead critical point.

In one embodiment, image data processing apparatus SP is programmed in a suitable scientific computing platform such as Matlab® and may be translated into C++ or C routines suitable to run on a computing system (such as the imager's workstation DPU).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for unwrapping phase shift data, comprising:
receiving phase shift data measured by a detector;
including the phase-shift data as parameters into a non-convex or non-concave objective function without a regularization term;
finding critical points of said objective function;
only among said critical points, finding a target critical point of a regularized objective function, said regularized objective function being formed from said objective function and a regularization term; and
outputting said target critical point as an estimate for unwrapped phase shift data.

2. A method for unwrapping phase shift data, comprising:
receiving phase shift data measured by a detector;
including the phase shift data as parameters into a regularized objective function formed from a non-convex or non-concave objective function and a regularization term;
finding critical points of said regularized objective function, said critical points including a lead critical point;
finding non-regularized critical points of said objective function without said regularization term;
choosing from among the non-regularized critical points so found, a target point that is closer to the lead critical point than at least one of the at least one other non-regularized critical point; and
outputting said chosen target point as an estimate for unwrapped phase shift data.

3. The method according to claim 1, wherein the objective function is derivable from a likelihood function in respect of the measured data.

4. The method according to claim 3, wherein an underlying probability density for the likelihood function is based on a wrapped Gaussian density.

5. The method according to claim 3, wherein an underlying probability density for the likelihood function is based on a von Mises density.

6. The method according to claim 1, wherein the regularization term is a Tikhonov regularizer.

7. The method according to claim 1, wherein in said method the phase shift data measured at a given pixel is processed independently from phase shift data measured at a neighboring pixel.

8. A signal processing apparatus configured to perform a method according to claim 1.

9. The signal processing apparatus according to claim 8, arranged for deriving the objective function from a likelihood function in respect of the measured data.

10. The signal processing apparatus according to claim 9, arranged for basing an underlying probability density for the likelihood function on a wrapped Gaussian density.

11. The signal processing apparatus according to claim 8, arranged for using a Tikhonov regularizer as the regularization term.

12. The signal processing apparatus according to claim 8, arranged for processing phase shift data measured at a given pixel independently from phase shift data measured at a neighboring pixel.

13. The signal processing apparatus according to claim 8, wherein the detector energy-resolving.

14. A computer program element for controlling a signal processing apparatus according to, which, when being executed by a data processing unit, is adapted to perform the method steps according to claim 1.

15. A computer readable medium having stored thereon the program element of claim 14.

* * * * *